United States Patent [19]

Reichle et al.

[11] Patent Number: 4,461,893

[45] Date of Patent: Jul. 24, 1984

[54] 1,3,5-TRIACRYLYLHEXAHYDRO-S-TRIAZINE DERIVATIVES

[75] Inventors: Walter T. Reichle, Warren; Louis B. Conte, Jr., Newark, both of N.J.

[73] Assignee: Union Carbide Corporation, Danbury, Conn.

[21] Appl. No.: 363,561

[22] Filed: Mar. 30, 1982

[51] Int. Cl.³ .......................................... C07D 251/04
[52] U.S. Cl. ...................................... 544/215
[58] Field of Search ........................................... 544/215

[56] References Cited

U.S. PATENT DOCUMENTS

| | | | |
|---|---|---|---|
| 2,559,694 | 7/1951 | Zerner et al. | 260/88.1 |
| 2,559,835 | 7/1951 | Zerner et al. | 260/248 |
| 3,016,281 | 1/1962 | Kropa et al. | 8/116.2 |
| 3,400,127 | 9/1968 | Tesoro et al. | 260/248 |
| 3,438,984 | 4/1969 | Hoffman | 260/248 |
| 3,518,265 | 6/1970 | Beears | 260/248 |
| 3,665,004 | 5/1972 | Ashton et al. | 260/248 |
| 3,736,320 | 5/1973 | Karustis, Jr. | 260/248 |

*Primary Examiner*—John M. Ford
*Attorney, Agent, or Firm*—William E. Dickheiser; Henry H. Gibson

[57] ABSTRACT

Derivatives of 1,3,5-triacrylylhexahydro-s-triazine formed by the reaction of acrylonitrile and acrylonitrile derivatives with a compound affording formaldehyde and/or acetaldehyde, demonstrate reinforcement promotion ability comparable that of to 1,3,5-triacrylylhexadro-s-triazine, coupled with enhanced solubility in organic solvents.

12 Claims, No Drawings

1,3,5-TRIACRYLYLHEXAHYDRO-S-TRIAZINE DERIVATIVES

This invention is directed to derivatives of 1,3,5-triacrylylhexahydro-s-triazine (TAHT) and a process for the preparation thereof. Unlike TAHT, these derivatives are readily soluble in certain organic solvents and are thus more easily applied as solutions to inorganic fillers, such as clay, prior to their use as filler-polymer coupling agents. Clay-loaded polymers which are produced using these novel TAHT derivatives exhibit desirable impact and tensile properties.

The use of 1,3,5-triacrylylhexahydro-s-triazine as a reinforcement promoter is disclosed in U.S. patent application Ser. No. 295,811 filed on Aug. 27, 1981. Similarly, Japanese Patent Application Public Disclosure No. 133438/1980, disclosed on Oct. 17, 1980, relates to polyolefinic resin compositions containing 1,3,5-triacrylylhexahydro-s-triazine.

A major problem faced when TAHT is employed as a reinforcement promoter is that this compound is only slightly soluble in water and in many of the common organic solvents, as seen in Table I below (a process for producing TAHT in solution of up to 10 weight percent utilizing methylene chloride as a solvent is disclosed in U.S. Patent Application Ser. No. 363,108 filed on Mar. 29, 1982 now U.S. Pat. No. 4,413,133 (Conte, Jr. et al.). Therefore, it is difficult to achieve uniform TAHT dispersion throughout the filler-polymer mixture. Current technology (see Japanese Disclosure No. 133438/1980, supra) requires that the TAHT be (1) either finely ground and mixed in a solid form with the inorganic filler or (2) suspended in water, alcohol, acetone or other organic solvent for spraying. Thus application of TAHT as a solid requires costly grinding and mixing steps as well as the use of greater amounts of expensive TAHT to ensure sufficient dispersion throughout the inorganic filler. Liquid application requires the use of large amounts of solvent with the accompanying expenses of both solvent cost and solvent removal. Thus there is an evident need for compounds which are readily soluble in organic solvents and which also possess the reinforcement promotional abilities of TAHT.

TABLE I
SOLUBILITY OF TAHT

| SOLVENT | WEIGHT % TAHT SOLUBLE AT 28° C. |
|---|---|
| water | approximately 0.8 |
| methanol | 4.0 |
| ethanol | 2.7 |
| acetone | 6.3 |
| aliphatic hydrocarbons | .0 |
| carbon tetrachloride | .0 |
| methylene chloride | 11-12 |

The derivatives of 1,3,5-triacrylylhexahydro-s-triazine which are contemplated by the instant invention are represented by Formula I below:

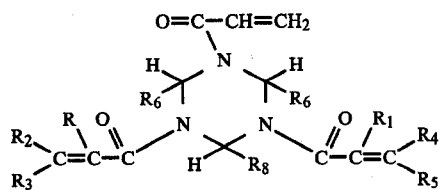

Formula I wherein R and $R_1$ are each independently hydrogen, chlorine, cyanide, or $C_1$ to $C_3$ straight chain or branched alkyl; $R_2$, $R_3$, $R_4$ and $R_5$ are each independently hydrogen, phenyl, or $C_1$ to $C_5$ straight chain or branched alkyl; and $R_6$, $R_7$ and $R_8$ are each independently hydrogen or methyl; with the proviso that when $R_2$, $R_3$, $R_4$, $R_5$, $R_6$, $R_7$, $R_8$ and R are hydrogen, $R_1$ is not hydrogen.

The preferred compounds of this invention contain reactive carbon-carbon double bonds, to the extent that such compounds possess an inequality value (I) in excess of about 2.5, such inequality value being defined by the Equation:

Equation I $$I = 6Q(e+2)(1-2R_F^\circ)$$

wherein Q and e are the Alfrey-Price parameters for the particular carbon-carbon double bonds, and $R_F^\circ$ is the flow-rate ratio relative to that of di-n-butyl fumarate as determined by chromatography using neutral silica as the substrate and xylene as the coherent.

With respect to Equation I, supra, the parameters Q and e are commonly used for characterizing the resonance and the polarity effects, respectively, in the copolymerization of monomers. A detailed description of the Q, e concepts are given by T. Alfrey, Jr. and L. J. Young in Chapter 2, pages 67-87 of G. E. Ham (ed): *Copolymerization*, Interscience (New York), 1964, and in the references listed at the end of this chapter. An extensive tabulation of Q, e-values for monomers is given by L. J. Young on pages II-387 to II-404 in the second edition of *Polymer Handbook*, edited by J. Brandrup and E. H. Immergut, Interscience (New York), 1975. The compounds defined here by the above generalized structural formula cannot in general be found in such tables; however, Q, e-values for potential reinforcement promoters may be estimated from the values for monomers having closely similar carbon-carbon double bond structures. The Q and e terms in the inequality reflect the experimental finding that Q-values should be high and that, generally, positive e-values are much more effective than are negative e-values.

The last parameter $R_F^\circ$ is a measure of the adsorptivity of a potential reinforcement promoter onto highly polar mineral surfaces. Many interactions between organic compounds and solid surfaces are highly specific, e.g., one mineral may result in chemical bonding, another mineral may result in adsorption, say, by dipole-/dipole interactions. However, for the purpose of this invention, the requirement of adsorptivity is for convenience expressed in terms of the adsorption of the compound from a xylene solution onto neutral silica gel using di-n-butyl fumarate as the standard. This is merely a convenient representation of a filler (silica) in a hydrocarbon polymer (xylene). The $R_F^\circ$ term assures that the potential reinforcement promoter molecule will adsorb sufficiently onto the filler surface so as to effectively contribute to the morphological change required in the polymer layer immediately adjacent to the filler particle. The chromatographic adsorption parameter $R_F$ is defined as the ratio of advancement of the dissolved compound relative to the advancement of the solvent front in a conventional thin-layer chromatography test. The $R_F°$ parameter used in the above equation is defined as the ratio of the $R_F$ value for the compound being tested relative to the $R_F$ value of the standard compound ($R_{FS}$):

$$R_F° = (R_F/R_{FS})$$

the standard selected here being di-n-butyl fumarate. As a general reference to chromatographic techniques and concepts, reference is made to L. R. Snyder, *Principles of Adsorption Chromatography*, Marcel Dekker, Inc. (New York), 1968. A specific reference on this layer plate techniques using particulate mineral coatings on glass plates is given by J. G. Kirchner, J. M. Miller and G. J. Keller in *Analytic Chemistry*, Vol. 23, pages 420-425, March 1951. The $R_F°$ term in the inequality states that the adsorptivity of an effective reinforcement promoter must be appreciably greater than that of di-n-butyl fumarate under the stated conditions.

The inequality is a statement of our findings that the parameters, Q, e and $R_F°$ should preferably simultaneously be within certain ranges of values and that some relaxation in the requirements for one or more parameters is favorable only if one or more of the other parameters assume particularly favorable values.

Particularly preferred compounds of the instant invention include compounds, i.e., 1,3-diacrylyl-5-methacrylylhexahydro-s-triazine and 1-acrylyl-3,5-dimethacrylylhexahydro-s-triazine, which may be represented by Formula II below:

Formula II

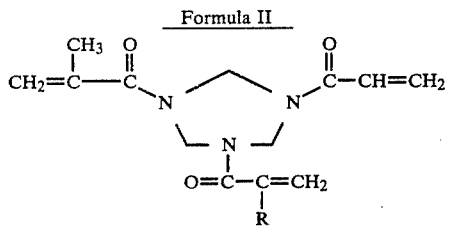

wherein R is hydrogen or methyl.

The compounds of the instant invention are prepared by reacting a mixture of acrylonitrile and acrylonitrile derivative with a substance which affords formaldehyde and/or acetaldehyde on decomposition, such as trioxane or mono-, di- or trimethyl substituted trioxane in an organic solvent in contact with a catalytic amount of an acid having a Hammet acidity function $(H_o)^1$ in excess of about 7.3.

[1] An explanation and listing of $H_o$ values is found in *The Chemist's Companion*, Arnold J. Gordon and Richard A. Ford, Wiley-Interscience.

The acrylonitrile derivatives which may be employed may be represented by Formula III below:

Formula III

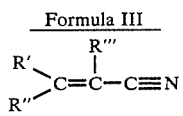

wherein R' and R" are each independently hydrogen, phenyl, or $C_1$ to $C_5$ straight chain or branched alkyl; and R''' is hydrogen, chlorine, cyanide or $C_1$ to $C_3$ straight chain or branched alkyl.

While not wishing to be held to any particular reaction mechanism, it is hypothesized that the reaction occurs according to the following sequence. The acid catalyst first cleaves the formaldehyde and/or acetaldehyde affording compound to produce formaldehyde and/or acetaldehyde:

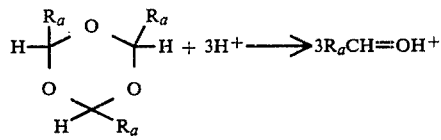

The nominally nucleophilic nitrile then attacks the aldehyde carbon to form an adduct which rearranges to form an acrylyl imide:

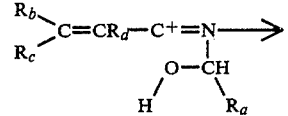

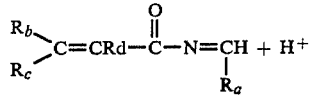

wherein $R_a$ is hydrogen or methyl; $R_b$ and $R_c$ are each independently hydrogen, phenyl or $C_1$ to $C_5$ straight chain or branched alkyl, and $R_d$ is hydrogen, chlorine, cyanide or $C_1$ to $C_3$ straight chain or branched alkyl.

These acrylyl imides are unstable and readily trimerize to form the 1,3,5-triacrylylhexahydro-s-triazine derivatives of the instant invention.

The reaction products of the above reaction sequence possess the reinforcement promotional properties of TAHT coupled with enhanced solubility in many common organic solvents.

The acrylonitrile:acrylonitrile derivative ratio employed in the reaction mixture may range from about 0.25:1 to about 4:1. However, ratios in excess of about 2:1 will result in the formation of lesser soluble TAHT as the primary product. Ratios below about 0.5:1 will result in the production of substantial amounts of compounds which do not possess an acrylyl substituent and which therefore do not possess as desirable reinforcement promotional properties as do TAHT or the TAHT-derivatives disclosed herein. Most preferably equal molar amounts of acrylonitrile and acrylonitrile derivatives should be employed.

The amount of formaldehyde and/or acetaldehyde affording compound charge can vary such that the ratio of (moles formaldehyde plus moles acetaldehyde):(moles acrylonitrile plus moles acrylonitrile derivate) is from about 0.5:1 to about 2:1. Preferably, however, such ratio is from about 1:1 to about 1.1:1.

The solvents that may be employed include any organic solvents in which the TAHT-derivatives produced will be soluble, and which are not reactive with the acid employed as the catalyst. Representative of such solvents are the saturated hydrocarbons such as hexane, heptane and the like, and chlorinated saturated hydrocarbons such as carbon tetrachloride, methylene chloride, and the like; and aromatic hydrocarbons such as toluene and the like. Hexane and heptane are the preferred solvents.

The solvent may be present in any amount, but for commercial practicality one prefers to produce as concentrated a product as possible.

The acid catalysts which may be employed are those which possess a Hammet acidity function ($H_o$) in excess of about 7.3. Representative of such acids are concentrated sulfuric acid, oleum and the like. Concentrated sulfuric acid is the preferred catalyst.

In order to minimize the formation of methylene-bis-amides, it is preferable to add a moisture scavenger and to keep reaction conditions as anhydrous as possible. Compounds well known to one skilled in the art, including organic anhydrides such as acetic anhydride and the like as well as inorganic anhydrides such as sulfur trioxide (in the form of oleum), phosphoric anhydride and the like, may be employed as the moisture scavenger. In addition, it is preferable to pretreat the solvent, e.g., by drying over a molecular sieve, in order to reduce its water content.

Further, it is also preferable to add small amounts of polymerization inhibitor to the reaction mixture in order to minimize polymer formation. Polymerization inhibitors well known to one in the art, such as, for example, hydroquinone, acetophenone, o-nitroaniline, m-nitroaniline, p-nitroaniline, n-nitroanisol, anthracene, diazoaminobenzene, o-dinitrobenzene, m-dinitrobenzene, 1,3,5-trinitrobenzene, benzophenone, p-benzoquinone, benzoyl chloride, diphenyl and the like may be employed. The amounts of moisture scavenger and polymerization inhibitor which may be added are not critical, and, in general, are limited only to the extent that the presence of these compounds interferes with the production of the TAHT derivatives of the instant invention.

The reaction is conducted at a temperature of from about 40° C. to about 130° C. with preferred temperatures ranging from about 60° C. to about 85° C.

The reaction is conducted at pressures of from about atmospheric (i.e., about 14.5 psi) to about 1000 psi with pressures of from about 25 psi to about 75 psi preferred.

Reaction time is not critical, and may vary from less than a few hours to several days or more depending upon the reaction batch size, temperature, pressure, etc., selected. However, it is preferable to conduct the reaction as quickly as heat removal (from the exotherm produced by the reaction of acrylonitrile with trioxane) allows.

The instant process may be conducted in a batch, semicontinuous, or continuous fashion by means apparent to one skilled in the art. It is preferable to periodically (if a continuous or semicontinuous mode is selected) or after each batch is complete (if a batch type mode is selected) to wash the apparatus with hot solvent in order to minimize byproduct buildup on the walls of the reactor.

One preferred embodiment of the instant invention involves the creation of mixed acrylonitrile (AN)/methacrylonitrile (MAN) compounds utilizing trioxane as the formaldehyde source and employing sulfuric acid as the catalyst.

In such embodiment, the acrylonitrile:methacrylonitrile ratio employed in the reaction mixture may range from about 0.25:1 to about 4:1. However, ratios in excess of about 2:1 will result in the formation of lesser soluble TAHT as the primary product, which is less desirable since the acrylyl moiety has a greater tendency to form polymers than does the methacrylyl moiety. Ratios below about 0.5:1 will result in the production of substantial amounts of the symmetrical 1,3,5-trimethacrylylhexahydro-s-triazine, which does not possess as desirable reinforcement promotional properties as does TAHT or the TAHT-derivatives disclosed herein. Most preferably equal molar amounts of acrylonitrile and methacrylonitrile should be employed.

The amount of trioxane charged should be such that a slight excess of moles of formaldehyde is present relative to the number of moles of (AN+MAN). Preferably the ratio of moles formaldehyde moles (AN+MAN) should be from about 1.01:1 to about 1.1:1.)

It should be noted that the reaction of acrylonitrile/methacrylonitrile with trioxane is exothermic. Thus, in order to control this exotherm, it is preferable to add a solution of trioxane and AN/MAN to a solution of AN/MAN and sulfuric acid catalyst at a rate low enough so that a constant controllable reflux is maintained.

EXAMPLES

The following examples serve to further illustrate the invention, they are not intended to limit the invention in any way.

A series of runs (Examples 1, 2, 3, 4, 5 and 6) was conducted using the solutions indicated in Table II below. A series of comparative runs (comparative Examples A, B and C) was also carried out.

Solution I was added to a 3-neck round bottom flask equipped with a mechanical stirrer, thermometer, reflux condenser (approximately 6-7 bulbs), dropping funnel and a hot and cold water bath, and maintained under a slight nitrogen stream. This solution was heated to the reaction temperature listed in Table III below and the dropwise addition of Solution II begun.

TABLE II

| Example | Solution I | | | | | | | Solution II | | | | | |
|---|---|---|---|---|---|---|---|---|---|---|---|---|---|
| | AN[1] | | MAN[2] | | Catalyst $H_2SO_4$ (96%) | Hydro-quinone | Solvent Hexane | | | | | Trioxane | | Solvent Hexane |
| | (gms) | (moles) | (gms) | (moles) | (gms) | (gms) | (ml) | (gms) | (moles) | (gms) | (moles) | (gms) | moles/$CH_2O$ | (ml) |
| 1 | 19.9 | 0.375 | 50.2 | 0.75 | 3.5 | 0.5 | 200 | 19.9 | 0.375 | 50.2 | 0.85 | 67.6 | 2.25 | 50 |
| 2 | 37.1 | 0.7 | 47.0 | 0.7 | 1.50 | 0.1 | 145 | 37.0 | 0.7 | 47.0 | 0.7 | 42.0 | 1.4 | 145 |
| 3 | 37.1 | 0.7 | 47.0 | 0.7 | 1.50 | 0.1 | 145 | 3.0 | 0.7 | 47.0 | 0.7 | 42.0 | 1.4 | 145 |
| 4 | 53.0 | 1.0 | 33.6 | 0.5 | 3.0 | 0.1 | 125 | 53.0 | 1.0 | 33.6 | 0.5 | 98.09 | 3.27 | 125 |
| 5 | 53.0 | 1.0 | 22.4 | 0.33 | 3.0 | 0.1 | 125 | 53.0 | 1.0 | 22.4 | 0.33 | 80.0 | 2.67 | 125 |
| 6 | 70.7 | 1.33 | 22.4 | 0.33 | 3.5 | 0.1 | 125 | 70.7 | 1.33 | 22.4 | 0.33 | 100.0 | 3.33 | 125 |
| A | 0 | 0 | 50.3 | 0.75 | 1.50 | 0.1 | 145 | 0 | 0 | 50.3 | 0.75 | 45.0 | 1.5 | 145 |
| B | 0 | 0 | 50.3 | 0.75 | 1.50 | 0.1 | 145 | 0 | 0 | 50.3 | 0.75 | 45.0 | 1.5 | 145 |

TABLE II-continued

| | Solution I | | | | | | | Solution II | | | | | |
|---|---|---|---|---|---|---|---|---|---|---|---|---|---|
| | AN[1] | | MAN[2] | | Catalyst H$_2$SO$_4$ (96%) | Hydro-quinone | Solvent Hexane | | | | | Trioxane | Solvent Hexane |
| Example | (gms) | (moles) | (gms) | (moles) | (gms) | (gms) | (ml) | (gms) | (moles) | (gms) | (moles) | (gms) | moles/ CH$_2$O | (ml) |
| C | 53.0 | 1.0 | 5.3 | 0.07 | 2.0 | 0.1 | 125 | 53.0 | 1.0 | 5.3 | 0.07 | 64.1 | 2.14 | 125 |

[1]Acrylonitrile
[2]Methacrylonitrile

The addition of Solution II was regulated so that refluxing did not occur above the third bulb of the condenser. The acrylonitrile/methacrylonitrile ratio varied as shown in Table III below.

After the reaction had been continued at reflux for the period indicated, the contents of the flask were cooled to 20° C. and discharged. The product was recovered by drying in a vacuum oven at room temperature (approximately 25°–30° C.). Table III summarizes the reaction conditions and product recovery.

grams of the triazine reinforcement promoter, indicated in Table IV, in enough methylene chloride to dissolve the promoter, but less than the amount of solvent which would produce a paste with the wetted filler. The triazine promoter solution was then added to 500 grams of filler, blended mechanically and air dried overnight.

The pretreated filler was compounded with 250 grams of thermoplastic polymer on a 6" by 12" 2-roll mill at 180° C. by adding 250 grams of pretreated filler incrementally to the fluxed polymer. Mixing was con-

TABLE III

ACRYLONITRILE-METHACRYLONITRILE REACTIONS

| Example | Molar Ratio AN[1]/MAN[2] | Reaction Temp. | Reaction Time (hrs) | % Conversion (Theoretical) | Solubility at Reflux Temp.[4] | Product | Mole Ratio AN:MAN Components in Triazine Product[3] |
|---|---|---|---|---|---|---|---|
| 1 | 1:2 | 66 | 4 | 87 | All | light tan product - cheesy when cold | — |
| 2 | 1:1 | 62 | 22 | 52.4 | All | gelled on roto-vac | — |
| 3 | 1:1 | 62 | 22 | 78.2 | All | light tan viscous liquid | 1.2:1 |
| 4 | 2:1 | 62 | 2 | 61.0 | Insol. | light tan powder | 1.9:1 |
| 5 | 3:1 | 63 | 18 | 84.8 | Insol. | light tan powder | 5.8:1 |
| 6 | 4:1 | 63 | 2 | 93.0 | Insol. | light tan powder | 6.1:1 |
| A | 0:1 | 66 | 22 | 62 | All | white powder | — |
| B | 0:1 | 66 | 22 | 62 | All | white powder | — |
| C | 14:1 | 63 | 5 | 80.0 | Insol. | light tan powder | 20:1 |

[1]AN = acrylonitrile
[2]MAN = methacrylonitrile
[3]As determined by Carbon-13 NMR analysis
[4]Visual observation The results in Table III indicate that when approximately equal amounts of acrylonitrile and methacrylonitrile are employed as starting material, a large proportion of the reaction product is a light tan liquid which is different from the product produced when the AN:-MAN ratio is above about 2:1. This light tan liquid was found to have enhanced solubility in hexane relative to the reaction products of Examples 5, 6 and C. (It must be noted, however, that Examples 5, 6 and C all produced smaller amounts of the TAHT derivatives of the instant invention, along with larger amounts of TAHT.)

In order to test the properties of the novel compounds as reinforcement promoters, clay-polymer compositions were produced comprising about 1 weight percent of triazine compound, about 50 weight percent high-density polyethylene (having a density of 0.959 g/cc and a melt index of 0.7) and about 49 weight percent of unmodified hard clay (consisting of a hydrated kaolin with a mean particle size of 0.3 μM and a B.E.T. surface area of 20 to 24 m²/g).

The procedure for making the treated, filled thermoplastic polymer compositions was as follows. The filler pretreatment procedure consisted of dissolving about 10 tinued using thorough compounding procedures. A sheet of the treated, filled polymer was then cut and rolled into a cylindrical bar, i.e., "pig", and then passed end-wise through the compounding mill about ten times for a total mixing time of ten minutes after all the filler had been added. The product composition was then sheeted off the mill, allowed to cool to room temperature and granulated.

The granulated product composition was injection molded at a melt temperature of 215° C. using a 38 cm³ capacity, 30 ton reciprocating screw-injection machine with a mold providing an ASTM dog bone test bar with dimensions of 2 inches by ⅛ inch by ⅛ inch for testing tensile properties, and a rectangular bar with dimensions of 5 inches by ½ inch by ⅛ inch for testing flexural properties. The following tests were used for each product composite:

| Tensile Strength | ASTM | D638-76 |
|---|---|---|
| Tensile Modulus | ASTM | D638-76 |
| Elongation at Break | ASTM | D638-76 |

| Izod Impact Strength | ASTM | D256-73 |

During the tension tests a cross-head speed of 0.2 inch per minute was utilized.

These compositions, containing reaction products produced by varying the acrylonitrile to methacrylonitrile ratios as reinforcement parameters, also exhibited varying properties. The AN/MAN ratios and properties are listed in Table IV.

TABLE IV

| Example | Ratio AN/MAN | Tensile Strength (psi) | Tensile Modulus (psi) | Elongation at Break (%) | Izod Impact Strength (ft-lbs/in.) |
|---|---|---|---|---|---|
| 7 | — | 3,610 | 292 | 4 | 0.6 |
| 8 | 1:0 (TAHT) | 5,040 | 354 | 40 | 3.4 |
| 9 | 4:1 | 4,900 | 352 | 46 | 3.5 |
| 10 | 3:1 | 4,870 | 353 | 38 | 3.6 |
| 11 | 2:1 | 4,700 | 358 | 50 | 2.8 |
| 12 | 1:2 | 4,930 | 350 | 18 | 2.2 |
| 13 | 0:1 | 4,510 | 382 | 5 | 1.3 |

This data indicates that the compounds of this invention, when used as reinforcement promoters, exhibit reinforcement promotional abilities nearly equal to that of TAHT, in addition to their enhanced (vis-a-vis TAHT) solubility. It is to be noted that Examples 9, 10, 11 and 12 all contain various amounts of the novel compounds of this invention, as indicated by the NMR data of Examples 1, 4, 5 and 6 in Table III.

We claim:

1. A compound of the formula:

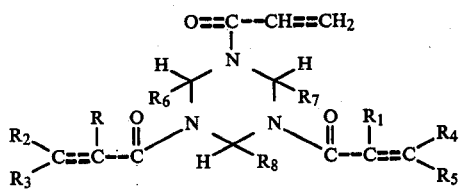

wherein
R and $R_1$ are each independently hydrogen, chlorine, cyanide, or $C_1$ to $C_3$ straight chain or branched alkyl; and $R_2$, $R_3$, $R_4$ and $R_5$ are each independently hydrogen, phenyl, or $C_1$ to $C_5$ straight chain or branched alkyl; and $R_6$, $R_7$, and $R_8$ are each independently hydrogen or methyl;

with the proviso that when $R_2$, $R_3$, $R_4$, $R_5$, $R_6$, $R_7$, $R_8$ and R are hydrogen, $R_1$ is not hydrogen.

2. The compound of claim 1 wherein R is hydrogen or methyl; $R_1$ is methyl; $R_2$, $R_3$, $R_4$, $R_5$, $R_6$, $R_7$ and $R_8$ are hydrogen.

3. The compound of claim 2 wherein R is hydrogen.

4. The compound of claim 2 wherein R is methyl.

5. Derivatives of 1,3,5-triacrylylhexahydro-s-triazine produced by reacting a mixture of acrylonitrile and acrylonitrile derivative of the formula:

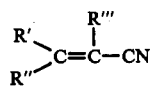

wherein R' and R'' are each independently hydrogen, phenyl, or $C_1$ to $C_5$ straight chain or branched alkyl; and R''' is hydrogen, chlorine, cyanide or $C_1$ to $C_3$ straight chain or branched alkyl; with a substance which affords formaldehyde and/or acetaldehyde on decomposition, at a temperature of from about 40° C. to about 130° C., at a pressure of from about atmospheric to about 1000 psi, in an organic solvent in contact with a catalytic amount of an acid having a Hammet acidity function $(H_o)$[1] in excess of about 7.3; wherein the ratio of acrylonitrile to acrylonitrile derivative is from about 0.25:1 to about 4:1.

6. The derivative of claim 5 wherein the ratio of acrylonitrile to acrylonitrile derivative is from about 0.5:1 to about 1:1.

7. The derivative of claim 5 wherein the substance which affords formaldehyde and/or acetaldehyde is unsubstituted or mono-, di- or trimethyl substituted trioxane.

8. The derivative of claim 7 wherein the trioxane is unsubstituted trioxane.

9. The derivative of claim 5 wherein R' and R'' are hydrogen and R''' is methyl, such that the acrylonitrile derivative is methacrylonitrile.

10. Derivatives of 1,3,5-triacrylylhexahydro-s-triazine, soluble in an organic solvent selected from the group consisting of saturated hydrocarbons, chlorinated saturated hydrocarbons and aromatic hydrocarbons, which derivatives have the formula:

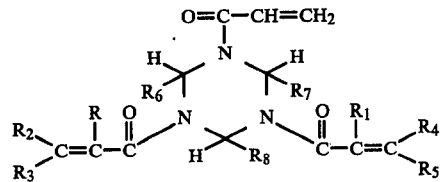

wherein $R_1$ are each independently hydrogen, chlorine, cyanide, or $C_1$ to $C_3$ straight chain or branched chain alkyl; $R_2$, $R_3$, $R_4$ and $R_5$ are each independently hydrogen, phenyl, or $C_1$ to $C_5$ straight chain or branched alkyl; and $R_6$, $R_7$ and $R_8$ are each independently hydrogen or methyl; with the proviso that when R, $R_2$, $R_3$, $R_4$, $R_5$, $R_6$, $R_7$ and $R_8$ are hydrogen, $R_1$ is not hydrogen; and wherein the ratio of acrylyl to acrylyl derivative components is from about 0.25:1 to about 4:1.

11. The derivatives of claim 10 wherein the ratio of acrylyl to acrylyl derivative components is from about 0.5:1 to about 1:1.

12. The derivatives of claim 10 wherein R is hydrogen or methyl; $R_1$ is methyl; $R_2$, $R_3$, $R_4$, $R_5$, $R_6$, $R_7$ and $R_8$ are hydrogen.

* * * * *